(12) United States Patent
Rubinstein et al.

(10) Patent No.: US 9,164,034 B2
(45) Date of Patent: Oct. 20, 2015

(54) DEVICE AND METHOD FOR OPTICAL LOCALIZED PLASMON SENSING

(75) Inventors: Israel Rubinstein, Rehovot (IL); Alexander Vaskevich, Rehovot (IL); Irit Ruach-Nir, Rehovot (IL); Tatyana Bendikov, Rehovot (IL)

(73) Assignee: YEDA RESEARCH AND DEVELOPMENT COMPANY LTD. AT THE WEIZMANN INSTITUTE OF SCIENCE, Rehovot (IL)

(\*) Notice: Subject to any disclaimer, the term of this patent is extended or adjusted under 35 U.S.C. 154(b) by 1219 days.

(21) Appl. No.: 12/478,895

(22) Filed: Jun. 5, 2009

(65) Prior Publication Data

US 2009/0257062 A1 Oct. 15, 2009

Related U.S. Application Data

(63) Continuation of application No. PCT/IL2007/001505, filed on Dec. 5, 2007.

(60) Provisional application No. 60/872,797, filed on Dec. 5, 2006.

(51) Int. Cl.
| | |
|---|---|
| G01N 33/553 | (2006.01) |
| G01N 21/552 | (2014.01) |
| B82Y 15/00 | (2011.01) |
| B82Y 30/00 | (2011.01) |

(52) U.S. Cl.
CPC .............. *G01N 21/554* (2013.01); *B82Y 15/00* (2013.01); *B82Y 30/00* (2013.01); *Y10T 428/24917* (2015.01)

(58) Field of Classification Search
None
See application file for complete search history.

(56) References Cited

U.S. PATENT DOCUMENTS

| | | | | |
|---|---|---|---|---|
| 5,527,712 | A * | 6/1996 | Sheehy | 436/525 |
| 2005/0244977 | A1 * | 11/2005 | Drachev et al. | 436/86 |

FOREIGN PATENT DOCUMENTS

WO 02/068943 A1 9/2002

OTHER PUBLICATIONS

Kambhampati et al., Novel silicon dioxide sol-gel films for potential sensor applications: a surface plasmon resonance study, 2001, Langmuir, 2001: pp. 1169-1175.*
Lacy et al., Characterization of SiO2-overcoated silver-island films as substrates for surface-enhanced raman scattering, 1996, Anal Chem, 68: pp. 1003-1011.*
Bao et al., Controlled layer-by-layer formation of ultrathin TiO2 on silver island films for surface-enhanced raman scattering measurement, 2004, Anal Chem, 76: pp. 4531-4536.*
International Search Report and Written Opinion, mailed Apr. 18, 2008, from International Application No. PCT/IL2007/001505, filed Dec. 5, 2007.
Doron-Mor, I. et al., "Ultrathin Gold Island Films on Silanized Glass. Morphology and Optical Properties," Chem. Mater. 2004, 16, 3476-3483.
Doron-Mor, I. et al, "Sensitivity of transmission surface plasmon resonance (T-SPR) spectroscopy: Self-assembled multilayers on evaporated gold island films," Chem. Eur. J. 2005, 11, 5555-5562.
Evans, C. et al., "Surface Modification and Patterning Using Low-Energy Ion Beams: Si—O Bond Formation at the Vacuum/Adsorbate Interface," Anal.Chem. 2002, 74, 317-323.
Haes, A. J. et al., "Plasmonic materials for surface-enhanced sensing and spectroscopy," MRS Bull. 2005, 30, 368-375.
Hashimoto, N. et al., "Cycle performance of sol-gel optical sensor based on localized surface plasmon resonance of silver particles," Science Direct, Sensors and actuators B 113 (2006) 382-388.
Hutter, E. et al., "Exploitation of localized surface plasmon resonance," Adv. Mater. 2004, 16, No. 19, 1685-1706.
Kalyuzhny, G. et al., "UV/Vis Spectroscopy of Metalloporphyrin and Metallophthalocyanine Monolayers Self-Assembled on Ultrathin Gold Films," J. Phys. Chem. B 2000, 104, 8238-8244.
Kalyuzhny, G. et al., "Differential plasmon spectroscopy as a tool for monitoring molecular binding to ultrathin gold films," J. Am. Chem. Soc. 2001, 123, 3177-3178.
Kalyuzhny, G. et al., "Transmission surface-plasmon resonance (T-SPR) measurements for monitoring adsorption on ultrathin gold island films," Chem. Eur. J. 2002, 8, No. 17, 3849-3857.
Kambhampati, D. K. et al., "Novel silicon dioxide sol-gel films for potential sensor applications: a surface plasmon resonance study," Langmuir 2001, 17, 1169-1175.
Lacy, W. et al., "Characterization of SiO2-overcoated silver-island films as substrates for surface-enhanced Raman scattering," Anal. Chem. 1996, 68, 1003-1011.
Lahav, M. et al., "Biological Sensing Using Transmission Surface Plasmon Resonance Spectroscopy," Langmuir 2004, 20, 7365-7367.
Liz-Marzan, L. M. et al., "Synthesis of nanosized gold-silica core-shell particles," Langmuir 1996, 12, 4329-4335.
Robertson, J. W. et al., "Insulating Ultrathin Silica Films Formed by a Room-Temperature Sol-Gel Process," Adv. Mater 2001, 13, No. 9, May 3, 662-667.
Ruach-Nir, I. et al., "Silica-stabilized gold island films for transmission localized surface plasmon sensing," J. Am. Chem. Soc., 2007, 129, No. 1, 84-92.
Thompson, W. R. et al., "Raman Spectroscopy of Covalently Bonded Alkysilane Layers on Thin Silica Films Immobilized on Silver Substrates," Anal. Chem. 66, 1994, 3362-3370.
Thompson, W. R. et al., "Thin Sol-Gel Silica Films on (3-Mercaptopropyl) trimethoxysilane—Modified Ag and Au surfaces," Chem. of Mater., 7, 1995, 130-136.
Thompson, W. R. et al., "Hydrolysis and Condensation of Self-Assembled Monolayers of (3-Mercatopropyl) trimethoxysilane on Ag and Au surfaces," Langmuir 1997, 13, 2291-2302.
Walls, D. J. et al., "Enhanced Raman Scattering at Dielectric Surfaces. 2. Molecular Orientations from Polarized Surface Raman Scattering," J. Phys. Chem. 1990, 94, 2039-2042.
Wanunu, M. et al., "Branched Coordination Multilayers on Gold," J. Am. Chem. Soc. 2005, 127, 17877-17887.

* cited by examiner

*Primary Examiner* — Chris L Chin
(74) *Attorney, Agent, or Firm* — Browdy and Neimark, PLLC (57) ABSTRACT

A device is presented comprising a multi-layer structure with a plurality of metal islands on the surface of a solid transparent substrate. The islands are coated by an ultrathin sol-gel derived silica film via self-assembled monolayer.

18 Claims, 10 Drawing Sheets

DEVICE AND METHOD FOR OPTICAL LOCALIZED PLASMON SENSING

RELATED APPLICATIONS

This application is a Continuation of International Application No. PCT/IL2007/001505, filed on Dec. 5, 2007, which in turn claims the benefit under 35 USC 119(e) of U.S. Provisional Application No. 60/872,797, filed on Dec. 5, 2006, both of which are incorporated herein by reference in their entirety.

FIELD OF THE INVENTION

This invention is generally in the field of chemical and biological sensors and relates to a sensing method and device based on localized plasmon optical sensing, particularly transmission localized surface plasmon sensing.

BACKGROUND OF THE INVENTION

The following references are considered to be pertinent for the purpose of understanding the background of the present invention:

(1) Hutter, E.; Fendler, J. H. Exploitation of localized surface plasmon resonance, *Adv. Mater.* 2004, 16, 1685.

(2) Kalyuzhny, G.; Vaskevich, A.; Schneeweiss, M. A.; Rubinstein, I. Transmission surface-plasmon resonance (T-SPR) measurements for monitoring adsorption on ultrathin gold island films, *Chem.-Eur. J.* 2002, 8, 3850.

(3) Doron-Mor, I.; Barkay, Z.; Filip-Granit, N.; Vaskevich, A.; Rubinstein, I. Ultrathin Gold Island Films on Silanized Glass. Morphology and Optical Properties., *Chem. Mater.* 2004, 16, 3476.

(4) Doron-Mor, I.; Cohen, H.; Barkay, Z.; Shanzer, A.; Vaskevich, A.; Rubinstein, I. Sensitivity of transmission surface plasmon resonance (T-SPR) spectroscopy: Self-assembled multilayers on evaporated gold island films, *Chem.-Eur. J.* 2005, 11, 5555.

(5) Wanunu, M.; Vaskevich, A.; Cohen, S. R.; Cohen, H.; Arad-Yellin, R.; Shanzer, A.; Rubinstein, I. Branched Coordination Multilayers on Gold, *J. Am. Chem. Soc.* 2005, 127, 17877.

(6) Liz-Marzan, L. M.; Giersig, M.; Mulvaney, P. Synthesis of nanosized gold-silica core-shell particles, *Langmuir* 1996, 12, 4329.

Various sensors making use of surface plasmon resonance such as biosensors, gas sensors, concentration sensors and ion sensors have been proposed in recent years.

The coupling of electromagnetic radiation to metal island films results, under certain condition, in enhanced extinction due to localized surface plasmon resonance (LSPR) scattering. Ultrathin gold films, prepared by evaporation of sub-percolation layers (typically up to 10 nm nominal thickness) onto transparent substrates followed by optional annealing, form arrays of well-defined metal islands with tunable wavelength of surface plasmon (SP) absorption band. As the SP band intensity and position are sensitive to the film morphology (island shape and inter-island separation) and the effective dielectric constant of the surrounding medium, such systems can be used for chemical and biological sensing in the transmission localized surface plasmon resonance (T-LSPR) mode. The localized SP coupling observed in dense assemblies of nanoparticles (NPs), either in solution or immobilized on solid substrates, introduces an additional factor which may strongly influences the conditions of the SP resonance.

Sensors based on localized SP resonance can be divided into two broad groups, namely, sensors based on monitoring changes in the dielectric constant of the immediate environment, and sensors based on changes in SP coupling. A combination of these effects was also exploited in localized SP sensing [1].

Changes in the localized SP band of discontinuous Au or Ag films upon analyte binding can be conveniently monitored using standard spectrophotometric equipment in the transmission mode, presenting a notable advantage in sensing applications. This method of transduction was termed transmission localized surface plasmon resonance (T-LSPR) spectroscopy [1, 2].

Some earlier works of the inventors have shown that ultrathin (typically not exceeding 10 nm nominal thickness) Au island films vapor-deposited onto transparent substrates display a SP extinction peak at 550-800 nm. The shape, intensity and position of the peak depend on the island morphology, determined by the evaporation conditions and post-deposition treatment [3]. Changes in the SP extinction band (intensity and wavelength of maximum absorbance) resulting from binding of various molecules to the Au islands were measured in the transmission mode [2]. A linear relationship existing between the surface coverage by adsorbing molecules, either bound directly to the Au or through a receptor layer, and the change in the SP intensity and wavelength [2], is useful for quantitative sensing. The T-LSPR spectroscopy was shown to be widely applicable, with a sensitivity which depends on the film preparation conditions [4].

WO 2002/068943, assigned to the assignee of the present application, discloses chemical detection and quantification methods and apparatus employing optical properties of ultrathin metallic films. According to this technique, detecting changes in surface plasmon intensity of an ultra-thin metallic film provides a quantitative indication of an adsorbed or non-adsorbed chemical substance.

SUMMARY OF THE INVENTION

The present invention is based on the realization that a major hindrance in use of sensing substrates that comprise a sensing surface with a plurality of islands of a noble metal, e.g. gold and silver, for sensing presence of an analyte in a medium, where the sensing is based on measurement of optical properties of the surface, is instability of the inherent optical properties of the surface upon exposure to an aqueous or organic media. For such sensing, it is desired that the change will be attributed primarily to the binding or removal of analyte to/from the T-LSPR based devices (transducers). Thus, the present invention provides substrates having islands of a (noble) metal on their surface covered by a thin silica film whereby the substrate has inherent stable optical properties, namely of no or minimal change in the optical properties, e.g. localized SP absorbance, following exposure to a medium, in particular organic solvents and aqueous solutions. The present invention also provides sensors based on such substrates. The changes in optical properties are essentially a consequence of binding or release of an analyte to/from the transducer surface.

The present invention solved the stability problem by providing a novel method for stabilizing a noble metal (e.g. Au) islands while maintaining a high sensitivity of the optical properties, e.g. determined by SP absorbance, to analyte binding. According to the invention, stabilization is achieved by coating the metal islands with an ultrathin silica layer in the range of 0.5-20 nm, typically 1-10 nm, and preferably about 1-3 nm thick.

The present invention provides, by first of its aspects, a device comprising a multi-layer structure with a plurality of metal islands on the surface of a solid transparent substrate, whereon said islands are coated by an ultrathin sol-gel derived silica film via self-assembled monolayer.

In some embodiments, the self-assembled monolayer is of a compound having the general formula (I)

$$Z\text{---}R\text{---}SiO_{x/2}(OH)_{3-x} \quad (I)$$

Z being a binding moiety that can chemically associate with, attach to, or chemically sorb onto the noble metal, and R is a linker moiety.

The present invention further provides, by another of its aspects, a process for manufacturing a sensing device, the process comprising:
(a) providing a solid transparent substrate with a plurality of metal islands on its surface;
(b) coating the islands with a monolayer of a compound having the general structure $$Z\text{---}R\text{---}SiO_{x/2}(OH)_{3-x}$$

Z being binding moiety that can chemically associate with, attach to, or chemically sorb onto the noble metal and R is a linker moiety; and
(c) immersing the monolayer-coated substrate in a medium comprising a silica-based sol-gel precursor and providing conditions for a sol-gel reaction to yield a silica film over said monolayer.

According to one embodiment of the invention, Z in formula (I) is a sulfur containing moiety, which can be adsorbed and made to firmly bind to a noble metal by a number of processes known per se.

Linker group R may, for example, be an aliphatic or aromatic moiety which may be optionally substituted, for example, by a carboxy, carbonyl, amino, hydroxy or thio group. As will be appreciated, the invention is not limited to the use of such linkers and any linking moiety permitting to obtain a relatively uniform monolayer on the surface of a noble metal substrate may be employed as linker R in accordance with the invention.

In some embodiments, the silica layer has a thickness in the range of about 0.5 to about 20 nm.

A particular example of a noble metal is gold. Other noble metals such as silver or gold-silver alloys as well as multi-metal core-shell structures may be used in accordance with the invention.

For use as a sensor, the surface of the silica film (to be referred to hereinafter at times as "sensing surface") is typically treated to permit binding of analytes with specified properties. Such surface treatment may include chemical treatment, for example, imparting an electrical charge onto the surface permitting binding of oppositely charged analytes; immobilizing specifically sensing moieties, typically such which are a member of a binding couple such as one of the couples including: antigen-antibody, sugar-lectin, receptor-receptor binding agent, biotin-avidin, nucleic acid strand-antisense strand, and others, whereby the device may serve for sensing the presence of the non-bound member of the couple.

At times, the sensing surface may already carry a priori bound analyte and medium properties may be determined through measurement of a change in optical properties as a result of their release of the bound analyte into the medium.

The sensing method of the invention may be qualitative or quantitative. In a quantitative sensing method, the concentration of a certain target analyte may determine the amount of bound analyte and the optical properties or a change versus baseline, may provide a measure of concentration of the analyte in the medium. In the case of a sensor device which contains a priori bound analyte, some of the bound analyte will be released into the medium until a steady state in which the release and the binding will be equal to one another, which equilibrium will depend on the level of the analyte in the medium. A quantitative sensing method may also be based on measurement of the rate of the change in optical properties from initial state until a state in which equilibrium has been reached.

The optical properties that are measured may be based on light transmission through the substrate, for which case the substrate should be made of a light transparent or translucent material, e.g. silica glass, titanium glass or glass of other materials; or light reflectance from the surface. The light transmission or reflectance that is measured may be absolute transmission or reflection, respectively, or preferably trough determination of transmission or reflection spectral profile. Specifically preferred is a measurement of transmission localized surface plasmon absorption.

The term "light" should be understood as encompassing near infrared, visible as well as near ultraviolet light, with light in the visible spectrum being preferred. The light source may be a broadband white light, laser, focused monochromatic light, etc.

The sensing surface throughout the device may be uniform in its analyte binding properties. Alternatively, the sensing surface may have a pattern of analyte binding properties with different locations binding different analytes. The latter is useful for multiplexing sensing of a variety of different analytes simultaneously.

The silica layer is deposited by a sol-gel procedure on the intermediate deposited molecular monolayer, e.g. an intermediate mercaptosilane monolayer. The silica coating may be prepared, for example, using a modified literature procedure employing change in the sol-gel reaction conditions achieved by elevating the reaction temperature to a temperature in the range of 40° C. to a temperature below the boiling temperature of the medium, e.g. in the range of 40-100° C., to shorten the silica film formation time from days to hours.

The inventors have found that metal islands benefit from an ultrathin inorganic coating. This is important if the device formed by such evaporated islands carrying substrate is to be used as a surface plasmon optical absorption based sensor. The higher adhesion is a useful property if the device is employed certain time after it has been fabricated. The higher adhesion thus enables longer shelf- and storage-life for the sensing device. The improved adhesion can be achieved by forming metal islands on the substrate surface by the evaporation procedures, rather than by metal nanoparticles' deposition.

In some embodiments the device has inherent stable optical properties and essentially unaffected following exposure to aqueous or organic solvents, washing and drying. The optical properties may be localized surface plasmon absorption. The changes in optical properties are essentially a consequence of binding or release of an analyte to/from a surface of the silica layer which may comprises analyte binding sites.

There is also provided a sensing device for sensing an analyte in a medium.

In some embodiments, the device is configured and operable as a transmission localized surface plasmon resonance (T-LSPR) recognition interface in which changes in the SP band are attributed exclusively to binding/release of analytes to/from the interface, enabling sensing applications. The device may be configured and operable as a sensor based on T-LSPR mode and the optical response of the sensor is sensitive to changes in the effective dielectric constant of the immediate environment. The sensor may be configured and operable as an optical transducer for chemical and/or biological sensing. The biological sensing may include label-free recognition of biological molecules using selective antibody-antigen interactions. The sensor may be an immunosensor configured and operable to selectivity differentiating between specific and nonspecific interactions. The silica layer is thin enough to afford high T-LSPR sensitivity, while the hydroxyl groups on its surface enable chemical modification for binding of receptor molecules.

Still further provided by a further aspect of the invention is a process for improving stability of surface optical properties of solid substrate carrying islands of a noble metal on its surface, the process comprising:
(a) coating the islands with a monolayer of a compound having the general structure Z being a binding moiety that can chemically associate with, attach to, or chemically sorb onto the noble metal and R is a linker moiety; and
(b) immersing the monolayer-coated substrate in a medium comprising a silica-based sol-gel precursor and providing conditions for a sol-gel reaction to yield a silica film over said monolayer.

In some embodiments, the coating is performed at temperature in the range of about 40° C. to about 100° C. The sol-gel precursor may be sodium silicate. The plurality of metal islands may be formed on the surface of the substrate by an evaporation procedure.

According to another broad aspect of the invention, there is provided a process for improving stability of surface optical properties of solid substrate carrying islands of a noble metal on its surface, the process comprising:
(a) coating the islands with a monolayer of a compound having the general structure Z being a binding moiety that can chemically associate with, attach to, or chemically sorb onto the noble metal and R is a linker moiety; and
(b) immersing the monolayer-coated substrate in a medium comprising a silica-based sol-gel precursor and providing conditions for a sol-gel reaction to yield a silica film over said monolayer.

The process maintains a high sensitivity of the surface plasmon absorbance to analyte binding.

The above and other features of the invention including various novel details of construction and combinations of parts, and other advantages, will now be more particularly described with reference to the accompanying drawings and pointed out in the claims. It will be understood that the particular method and device embodying the invention are shown by way of illustration and not as a limitation of the invention. The principles and features of this invention may be employed in various and numerous embodiments without departing from the scope of the invention.

BRIEF DESCRIPTION OF THE DRAWINGS

In the accompanying drawings, reference characters refer to the same parts throughout the different views. The drawings are not necessarily to scale; emphasis has instead been placed upon illustrating the principles of the invention. Of the drawings:

FIG. 1 is a schematic presentation of a device and stepwise procedure for preparation of ultrathin silica layers on Au island films. (a) Gold islands on silanized glass. (b) Formation of a 3-mercaptopropyl trimethoxysilane (MPTS) self-assembled monolayers (SAMs) on the gold surface. (c) Deposition of an ultrathin sol-gel silica film. Sizes of features in the scheme are not to scale.

FIG. 2 is a high-resolution X-ray Photoelectron Spectroscopy (XPS) spectra for the Si 2s peak at different stages of silica coating formation (a) Silica deposition at 23° C. on continuous, 100 nm Au film on silicon: 1—after formation of an MPTS SAM, 2—after 24 h in 1.5 w/% $SiO_2$ solution, 3—after 4 days in 1.5 w/% $SiO_2$ solution. (b) Deposition of a silica layer at 90° C. on continuous, 20 nm Au film on silanized glass: 1—after formation of an MPTS SAM, 2—after 2 h in 1.5 w/% $SiO_2$ solution.

FIG. 3 shows cyclic voltammetry (CV) results for ionic species at bare and silica-coated Au electrodes (silica deposited at 90° C. for 2 h), first cycle is always shown. (a) CV of $Fe(CN)_6^{3-/4-}$ carried out in 1 mM $K_3Fe(CN)_6+0.1$ M $Na_2SO_4$; 1—bare Au, 2—Au/$SiO_2$. (b) CV of $Ru(NH_3)_6^{3+/2+}$ carried out in 0.5 mM $Ru(NH_3)_6Cl_3+0.1$ M $Na_2SO_4$; 1—bare Au, 2—Au/$SiO_2$.

FIG. 5 shows extinction spectra recorded at different stages of preparation of multilayer structures on 5-nm-thick, annealed Au island films. (a) Silica coating: 1—bare Au; 2—after MPTS adsorption; 3—after silica deposition (at 90° C., 2 h). (b) Self-assembled coordination multilayer (from ref. [5]): 1—bare Au; 2—after SAM of bishydroxamate ligand; 3—after binding of Zr(IV) ions followed by a layer of hexahydroxamate ligand. (c) Normalized differential spectra derived from the data in a and b (obtained by subtraction of the spectrum of the bare Au, normalized to the peak intensity of the bare Au): 1—Au/bishydroxamate SAM; 2—Au/bishydroxamate SAM+Zr(IV)+hexahydroxamate layer; 3—Au/MPTS SAM; 4—Au/MPTS SAM+silica.

FIG. 6 shows a T-LSPR spectra (measured in air) of (a) bare Au island films (5 nm, annealed) and (b) coated with a silica layer (deposited at 90° C., 2 h), before and after 20 min immersion in various solvents: 1—before immersion, 2—after EtOH or MeOH, 3—after water, 4—after phosphate buffer saline (PBS).

FIG. 7 shows T-LSPR spectra (measured in air) for the binding of protoporphyrin IX (PPIX) to silica-coated (90° C., 2 h) Au island transducers. (a) Specific binding: 1—Au/silica+3-aminopropyl trimethoxysilane (APTS); 2—after PPIX binding; 3—difference spectrum (2-1); 4—spectrum of 4 µm PPIX solution in EtOH (optical path, 1 cm). (b) Nonspecific binding: 1—Au/silica; 2—after PPIX binding; 3—difference spectrum (2-1, scaled ×10).

FIG. 8 (a, b) are AFM and HRSEM images, respectively, of an Au/silica+APTS sample with a bound layer of Ag NPs. (c) TEM image of the citrate-stabilized Ag NPs. (d) Extinction spectra of: 1—Au/silica+APTS; 2—after binding of Ag NPs; 3—spectrum of Ag NPs in solution (spectra 1 and 2 were measured in air);

FIG. 9 represents transmission UV-vis spectra (solid lines: absolute, dashed lines: difference) for sensing specific and nonspecific antibody-antigen interactions. nonspecific interactions. dashed lines) for four different examples of antibody-antigen interactions specific binding (a) Rabbit-Anti-Rabbit, (b) Rabbit-Anti-Mouse, (c) Mouse-Anti-Mouse, (d) Mouse-Anti-Rabbit.

DETAILED DESCRIPTION OF THE PREFERRED EMBODIMENTS

The device of the present invention was characterized by UV-vis spectroscopy, ellipsometry, X-ray Photoelectron Spectroscopy (XPS), high-resolution scanning electron microscopy (HRSEM), atomic force microscopy (AFM) and cyclic voltammetry. It has been shown that the provision of an ultrathin silica coating stabilizes the optical properties of the Au island films toward immersion in water, phosphate buffer saline (PBS) and various organic solvents followed by washing and drying, thus providing proper conditions where the optical response is sensitive only to changes in the effective dielectric constant of the immediate environment. The silica layer is thin enough to afford high T-LSPR sensitivity, while the hydroxyl groups on its surface enable chemical modification for binding of receptor molecules. The use of silica-encapsulated Au island films as a stable and effective platform for T-LSPR sensing was demonstrated.

Preparation of noble metal (Au, Ag) island films with a stable optical response presents a challenging task. Development of a reliable platform for T-LSPR sensing requires nanoparticulate metal films showing stable and reproducible optical properties. Change in the optical properties of metal island films resulting from morphological changes occurring upon exposure to solvents and analytes as well as drying, introduces uncertainty in the detection.

The present invention is based on the understanding of the following: The substantial instability of metal islands, especially Au, on common substrates (glass, transparent oxides) causes changes in the SP coupling and influences the spectrum shape. The inventors have addressed this problem by evaporation of Au on mercaptosilane-modified glass substrates and modification of the annealing conditions [3]. The latter allows optimization of the optical response without substantially compromising the island adhesion to the glass. Despite the improved adhesion, the optical response of the Au island films remains sensitive to immersion in solvents followed by drying (measurements were carried out in air before and after immersion in a given solvent).

The sensitivity of the optical properties of Au and Ag island films to interaction with solvents is well known. It is assumed that changes in the optical response result from structural instability of the islands in solvents, reflecting interplay between the island surface energy and interaction with the substrate. For the development of T-LSPR based devices (transducers), a general approach to stabilization of the morphology and optical response of metal island films is therefore required.

In the present invention, the optical properties of Au island films prepared by evaporation onto silanized glass substrates were stabilized toward immersion in solvents and drying by coating the islands with an ultrathin sol-gel derived silica film. The limited distance sensitivity of T-LSPR measurements (a few tens of nanometers in optimized systems [4]), combined with the relatively thick recognition interfaces applied in biosensing, require minimization of the silica film thickness to preserve transducer sensitivity. The two-step method presented here includes self-assembly of a monolayer of 3-mercaptopropyl trimethoxysilane (MPTS) on the Au islands, followed by deposition of an ultrathin (ca. 1.5 nm) silica layer from a sodium silicate solution adjusted to a pH low enough to promote polymerization of the silicate groups.

Carrying out the deposition reaction at 90° C. rather than at room-temperature as in the published procedure [6] shortens the time necessary for formation of the silica shell from days to hours, without affecting the coating quality. Growth of the silica layer was monitored by UV-vis spectroscopy, ellipsometry and XPS measurements, while the surface morphology and blocking properties of the layer were characterized by high-resolution scanning electron microscopy (HRSEM), atomic force microscopy (AFM) and cyclic voltammetry (CV). Use of silica-coated Au island films as stable and effective T-LSPR transducers is demonstrated by monitoring changes in the optical response upon binding of Protoporphyrin IX and Ag NPs to a receptor layer on the silica surface.

EXAMPLES

Various examples were carried out to prove the embodiments claimed in the present invention. Some of these experiments are referred hereinafter. The examples describe the manner and process of the present invention and set forth the best mode contemplated by the inventors for carrying out the invention, but are not to be construed as limiting the invention.

Example 1

The following example details the materials and method used to provide substrates having islands of a (noble) metal on their surface covered by a thin silica film whereby the substrate has inherent stable optical properties, when immersed in a medium, in particular organic solvents and aqueous solutions, then washed and dried.

The chemicals used include the following:

Sodium silicate solution (27 w/%), 3-mercaptopropyl trimethoxysilane (MPTS), 3-aminopropyl trimethoxysilane (APTS), protoporphyrin IX (PPIX) and $Ru(NH_3)_6Cl_3$ (purchased from Aldrich).

Methanol and ethanol, absolute, analytical grade (purchased from J. T. Baker) were used;

ion-exchanger Amberlite IR-120 (purchased from Merck); $K_3Fe(CN)_6$, analytical (purchased from BDH chemicals);

Phosphate buffer saline (PBS) solution was prepared by tenfold dilution of commercial reagent GIBCO D-PBS(10×) —$CaCl_2$, —$MgCl_2$ (Invitrogen) with triply-distilled water.

Extinction spectra at normal incidence were measured in air using a Varian Cary 50 UV/VIS spectrophotometer. The wavelength scan range was 350-1000 nm and the scan speed was 600 nm·min$^{-1}$. The samples were placed in a special holder enabling transmission measurements of the same spot on the slide during all experimental stages.

Cyclic voltammetry (CV) was carried out with two redox probes: $Fe(CN)_6^{3-}$ (1 mM) and $Ru(NH_3)_6^{3+}$ (0.5 mM) in 0.1 M sodium sulfate solution. Experiments were performed in a three-electrode cell with a $K_2SO_4$-saturated $Hg/Hg_2SO_4$ reference electrode and a Pt counter electrode. Before each experiment the solution was deaerated by bubbling high-purity $N_2$, while during the CV an inert environment was maintained by passing $N_2$ above the solution. The CV always started at the most positive potential and the scan rate was 0.05V·sec$^{-1}$. The electrochemical measurements were carried out using (bare or silica-coated) 20-nm-thick, continuous Au films on silanized glass slides. The slides were partially immersed in the electrolyte solution; after completion of the experiment and emersion from the solution, the electrode area (ca. 0.5 cm$^2$) was determined using the clearly seen wetting line.

Ellipsometric measurements were carried out with a Rudolph Research Auto-EL IV null ellipsometer, at an angle of incidence $\phi+=70°$ and a wavelength $\lambda=632.8$ nm. The same four points were measured on each sample before and after film formation.

Atomic force microscopy (AFM) images were recorded in air using a PicoSPM instrument (Molecular Imaging, USA) operated in the acoustic AC (AAC) mode. The cantilevers used were NSC12 series of ultrasharp silicon (MikroMasch, Estonia), with a resonant frequency of 100-200 kHz and an average tip radius not exceeding 10 nm.

X-ray photoelectron spectroscopy (XPS) measurements were carried out using a Kratos Axis-HS XPS system, with a monochromatized Al K$\alpha$ X-ray source (1486.6 eV). For Si high-resolution analysis the Si 2s was chosen rather than the Si 2p region due to interference of the latter with the intense Au 4f peak.

High-resolution scanning electron microscope (HRSEM) images were obtained using a JSM-6700F high-resolution scanning electron microscope with a cold field emission electron source and an upper built-in SE detector. Low-energy SE signal suppression was performed to reduce the charging effect in the SE images.

Glass substrates for Au evaporation were cut from glass microscope cover slides (Deckglaser No. 2) into 18×9 mm pieces and cleaned using one of the following procedures: (i) the glass slides were immersed twice in fresh "piranha" solution (1:2 $H_2O_2$:$H_2SO_4$) for 20 min, followed by washing 3 times in triply distilled water and 3 times in methanol; (ii) the slides were immersed in fresh "piranha" solution for 1 h followed by treatment in hot (70° C.) solution of 1:1:5 $H_2O_2$:$NH_4OH$:$H_2O$ for 1 h and extensive rinsing in methanol. Pirahna solution reacts violently with organic materials and should therefore be handled with extreme care. The two pretreatment proceduret produced similar results. After cleaning, the glass slides were modified with APTS by overnight immersion in a 10 v/% APTS solution in methanol. The silanized glass slides were sonicated 3 times in methanol, washed with ethanol and dried under a stream of nitrogen, then transferred to the evaporation chamber. Silicon wafers were cut to 20×10 mm slides, immersed twice in fresh "piranha" solution for 20 min, immersed in hot (70° C.) solution of 1:1:5 $H_2O_2$:$NH_4OH$:$H_2O$ for 20 min, washed 3 times in triply distilled water and 3 times in methanol. The Si/SiO$_2$ slides were then left in a 10 v/% APTS solution in methanol for 3 h. The silanized silicon slides were sonicated 3 times in methanol and washed with ethanol, dried under a stream of nitrogen and mounted in the evaporation chamber. Au evaporation on glass or silicon substrates was carried out in a cryo-HV evaporator (Key High Vacuum) equipped with a Maxtek TM-100 thickness monitor. Homogeneous deposition was achieved by moderate rotation of the substrate plate. Au (99.99%, Holland-Moran, Israel) was evaporated from a tungsten boat at 2-4 µTorr. For preparation of Au island films on glass, a low deposition rate of 0.01 nm s$^{-1}$ was applied. Continuous, 20-nm-thick Au films on glass and 100-nm-thick Au films on Si/SiO$_2$ were deposited at a rate of 0.1 nm s$^{-1}$. Post-deposition annealing of Au-covered slides was carried out in air at 200° C. for 20 h using a Ney Vulcan 3-550 furnace. The heating rate was 5° C. min$^{-1}$ and the annealed slides were left to cool in air to room-temperature. The annealing temperature was chosen to maintain good adhesion of the Au to the substrates, provided by the organic silane monolayer [3]. The continuous Au films (20 nm on glass, 100 nm on silicon) provide smooth, (111) textured surfaces suitable for common characterization techniques (ellipsometry, electrochemistry, XPS, etc.).

The thin (ca. 1.5 nm) silica layers used for stabilizing the optical response of Au island films were deposited by generally following the method described by [6] with certain modifications.

Figure 1A:
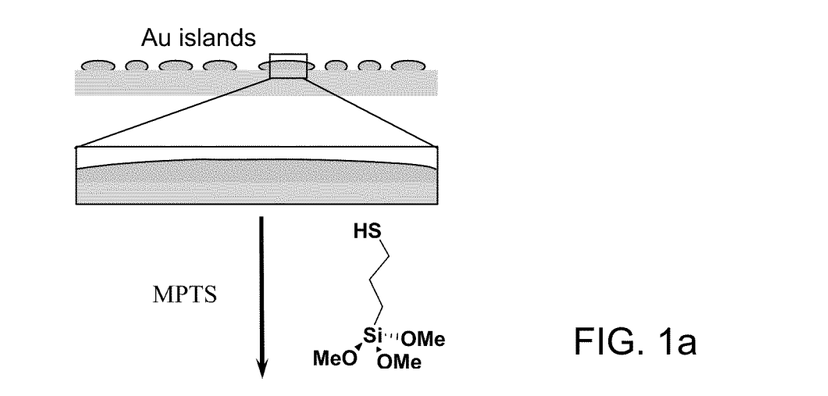
Figure 1B:
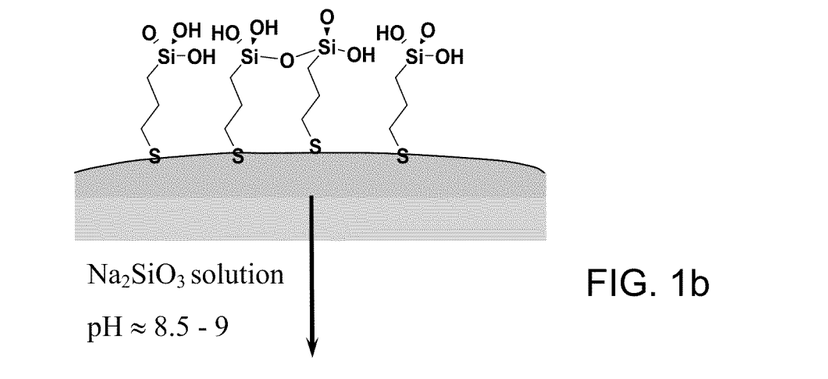
Figure 1C:
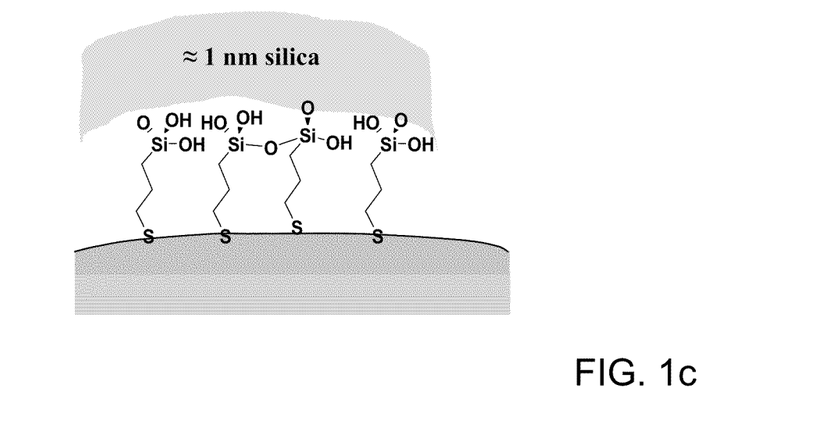

The general scheme of a sensing device of the present invention and the silica layer deposition used therein is exemplified in FIG. 1. It should be noted that the sizes of features in the scheme are not to scale. Au-coated glass slides, annealed, were washed in ethanol for 20 min and dried under a stream of nitrogen. The slides were then immersed for 1 h in a freshly-prepared solution of 2 mM MPTS in ethanol, washed for 20 min in ethanol and dried under a stream of nitrogen, to obtain an MPTS primer monolayer on the Au.

Sodium silicate solution (~1.5 w/% SiO$_2$, pH~12) was prepared by dilution of 2 ml of the original solution (27 w/% SiO$_2$) with triply-distilled water to a final volume of 50 ml. The strongly acidic cation exchanger Amberlite IR-120 was used for further adjustment of the solution pH to 8.5-9. For silica deposition the slides were then dipped for a certain time period in a 1.5% sodium silicate solution kept at a predetermined constant temperature. After removal from the sodium silicate solution, the silica-coated Au substrates were washed with water and dried under a stream of nitrogen. Transmission UV-vis spectra were measured in each step of the transducer preparation.

In the case of continuous Au films (20 nm or 100 nm thick), the silica coating procedure was preceded by 10 min UV-ozone treatment, 20 min ethanol dip and drying under a stream of nitrogen. Formation of silica coatings on continuous Au films was monitored by ex-situ ellipsometry. The ellipsometric thicknesses were calculated using typical values of a silica film optical properties $n_f=1.50$, $k_f=0$.

Stability tests were carried out on 5 nm Au island films coated with silica (prepared at 90° C. for 2 h). The stability of the Au plasmon peak was tested by immersion in four different solvents: ethanol, methanol, water and PBS followed by washing (for PBS) and drying under a stream of nitrogen. Spectra were measured in air, before dipping and after dipping and drying. In this mode of measurement change in the SP absorbance due to the different dielectric environment (solvent) is eliminated, leaving only structural effects. After obtaining the initial transmission UV-vis spectrum the sample was dipped in a given solvent for 20 min, removed and dried under a stream of nitrogen. In the case of PBS, after 20 min immersion the sample was washed with water before drying with nitrogen. After drying the final UV-vis spectrum was measured.

Then, binding of Protoporphyrin IX (PPIX) and Ag nanoparticles (NPs) was carried out. This was implemented as follows: 5 nm Au island films coated with a silica layer (prepared at 90° C. for 2 h) were washed in methanol for 20 min, dried under a stream of nitrogen, and left overnight in a solution of 10 v/% APTS in methanol. The samples were washed 3 times in methanol, then washed in ethanol and dried under a stream of nitrogen. This procedure provides an amine-terminated silica surface capable of electrostatic binding of negatively-charged species. For immobilization of the dicarboxylic acid porphyrin PPIX the amine-terminated samples were left in a saturated solution (0.2 mM) of PPIX in ethanol overnight, washed with ethanol and dried with nitrogen. A spectrum of PPIX dissolved in ethanol was taken at 4 µM concentration. For Ag NP binding, silica-coated Au island films with an APTS overlayer were dipped overnight in a solution of citrate-stabilized Ag NPs, washed with water and dried under a stream of nitrogen. Citrate-stabilized Ag NPs were prepared using a standard procedure.

The growth of silica layers on continuous Au substrates according to the methods described above was followed by ex-situ ellipsometry. The kinetics of silica layer formation was monitored by measurement of the ellipsometric parameter $\Delta$ at different times of immersion in sodium silicate solution. The total thickness of the ovelayer comprising a silica film on a mercaptosilane monolayer was calculated assuming formation of a uniform layer with a refractive index $n_f=1.5$, $k_f=0$. In experiments performed at room-temperature (23° C.), a limiting film thickness of ~1.1 nm was reached after 72 h. Further growth was extremely slow.

In order to achieve faster deposition, silica layer formation was carried out at higher temperatures (40° C.-90° C.), showing substantial acceleration of the kinetics. After 1 h of silica deposition at 90° C. under otherwise similar conditions the thickness of the overlayer was ~1.0 nm, while a silica layer thickness of 1.4-1.5 nm was reached after 1.5-2.0 h deposition. The latter immersion time (2 h) was chosen for the preparation of silica overlayers on Au island films. As shown below, the thickness of the silica layer formed on Au islands is similar to that measured ellipsometrically on continuous Au substrates.

Figure 2A:
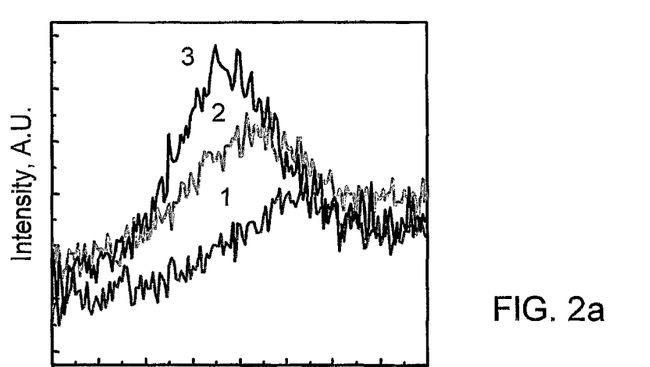
Figure 2B:
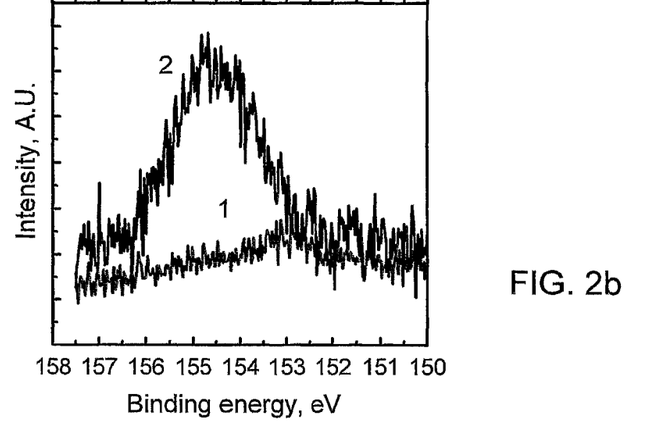

The surface elemental composition of slides at different stages of silica coating on continuous Au films was probed by XPS. FIG. 2 shows high-resolution scans in the Si 2s region for samples with an MPTS SAM and a silica layer grown at different temperatures. An increase in the area under the Si 2s peak and a shift to a higher binding energy are observed as the silica layer is formed. The energy shift reflects the deposition of $SiO_2$ (higher oxidation state) on the MPTS. For samples prepared at 90° C., the ratio O/Si is 3.0 after MPTS formation, decreasing to 2.53±0.29 after silica coating (2 h). The former value is in agreement with the 3:1 stoichiometric O:Si ratio in MPTS, while the decrease in the O/Si ratio reflects the formation of a silica layer with a stoichiometric O:Si ratio of 2:1 on the MPTS SAM. A similar change in the O:Si ratio from 3.7 for Au/MPTS to 2.6 for Au/MPTS/silica (steady state) was observed for samples prepared at 23° C. Hence, the XPS results are consistent with the formation of an ultrathin overlayer of $SiO_2$ upon immersion of Au/MPTS in sodium silicate solution.

Figure 3A:
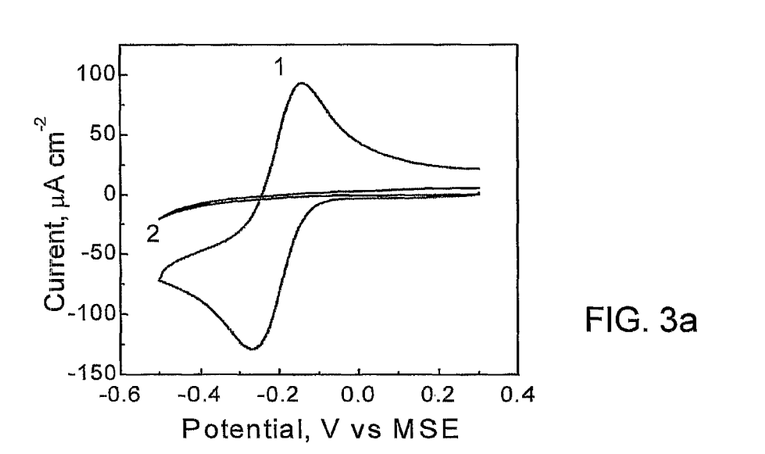

Sol-gel silica films are known to be nanoporous. Cyclic voltammetry (CV) of the charged redox probes $Fe(CN)_6^{3-/4-}$ and $Ru(NH_3)_6^{3+/2+}$ in neutral (pH~7) solution was used to characterize the blocking properties of silica layers deposited on continuous Au films. Comparison of CVs at bare and silica-coated Au electrodes illustrated in FIG. 3 reveals distinct differences in the access of negative and positive electroactive ions to the underlying electrode. The electrochemical response of $Fe(CN)_6^{3-}$ at an Au electrode coated with a silica layer deposited at 90° C. shows complete blocking of the electrode reaction of the anionic probe (FIG. 3a, line 2). The cationic redox probe $Ru(NH_3)_6^{3-}$ (FIG. 3b) shows a totally different behavior, i.e., the CV at the silica-coated electrode is nearly identical to that at the bare Au electrode (the current is slightly enhanced, see below), exhibiting essentially free access of the cationic species to the electrode.

Figure 3B:
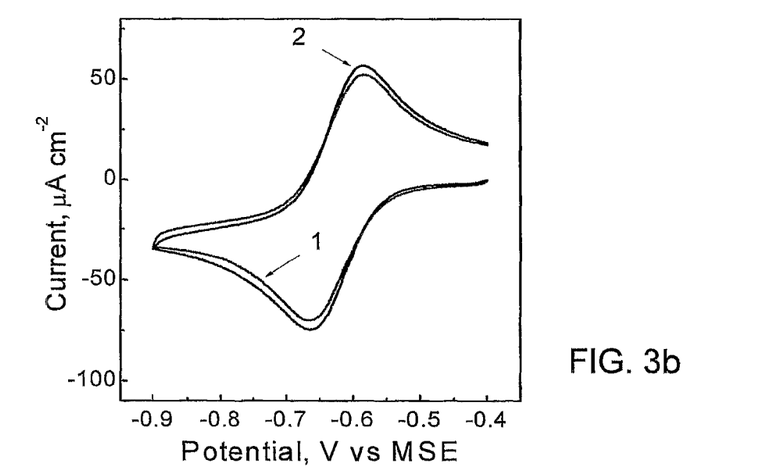

The permeability of ionic redox probes through silica layers is strongly influenced by electrostatic interactions. The point of zero charge (pzc) of sol-gel derived silica is around pH 2-4, therefore at the neutral pH applied here the silica layer is negatively charged. The negative silica surface charge furnishes an efficient electrostatic barrier to transport of the negatively-charged $Fe(CN)_6^{3-}$ ions, hence the effective blocking observed in the CV (FIG. 3a). On the other hand, the positively-charged $Ru(NH_3)_6^{3+}$ ions experience free access through the nanoporous silica layer (FIG. 3b). The small increase in the peak current for $Ru(NH_3)_6^{3+}$ is attributed to some accumulation of positively-charged ions in the silica pores. This minor effect is not detected when the electrode is transferred to background solution.

As shown above, ultrathin (ca. 1.5 nm) silica layers grown at 90° C. on continuous Au substrates exhibit excellent integrity. Next, the same scheme was applied to the deposition of similar silica layers on discontinuous, Au island films. The substrates used were 5.0 nm (nominal thickness) Au island films, annealed. These substrates were previously shown by the inventors to display superior distance sensitivity in T-LSPR spectroscopy [4]. It should be noted that experiments with 2.5 nm (nominal thickness) Au island films (not shown here) produced similar spectroscopic results.

The morphology of silica coatings on 5.0 nm Au island films was studied by AFM and HRSEM (FIG. 4). The Au islands in the AFM images appear larger in diameter, more rounded and closer to each other compared to the corresponding HRSEM images, resulting from tip convolution. The combined AFM and HRSEM data provide the accurate 2D shape of the Au islands at different stages (HRSEM), together with viable information on differences in the surface morphology affected by the silica coating (AFM).

Figure 4A:
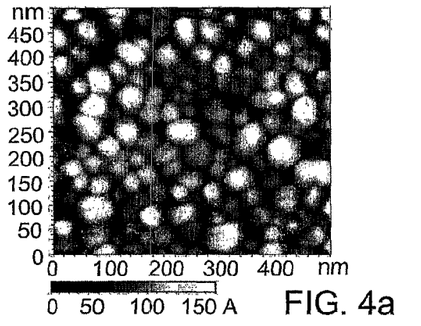
FIG. 4 shows an atomic force microscope (AFM) (a-c, 500×500 $nm^2$) and high resolution scanning electron microscope (HRSEM) (d-f, same length scale) images of 5 nm Au island films, annealed, at different stages of surface modification: (a,d) Bare Au; (b,e) after assembly of a 3-mercaptopropyl trimethoxysilane self-assembled monolayer (MPTS SAM); (c,f) after silica deposition (at 90° C., 2 h).
Figure 4B:
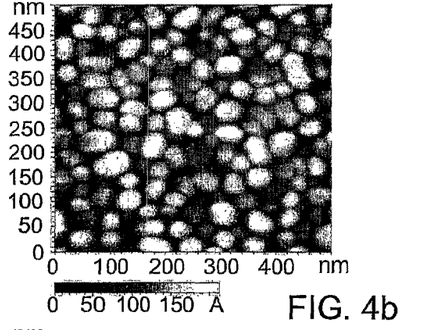
Figure 4C:
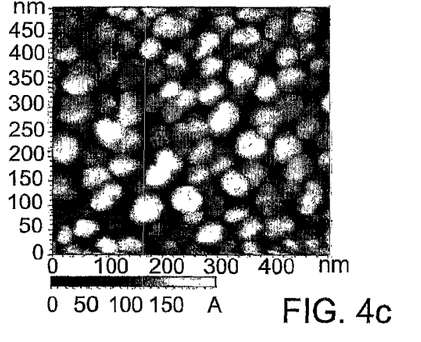
Figure 4D:
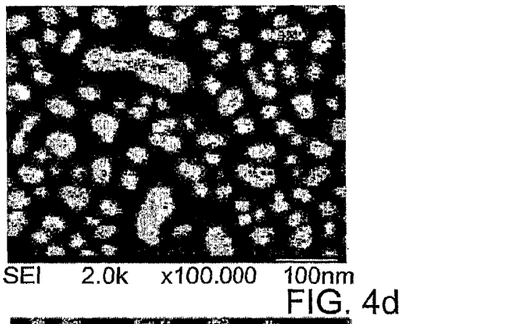
Figure 4E:
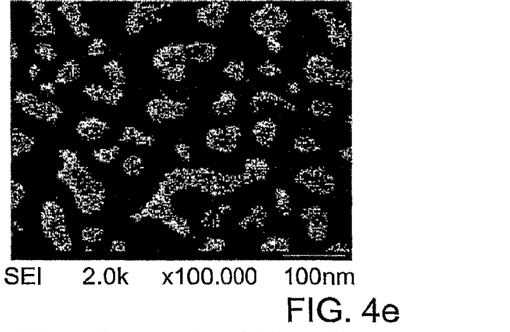
Figure 4F:
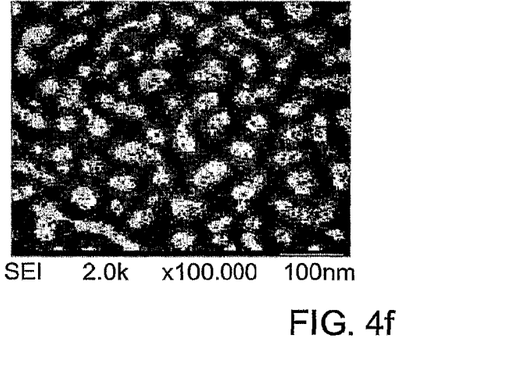

AFM images before and after MPTS adsorption are indistinguishable (FIG. 4a, b), as expected for binding of a monolayer. Coating with the silica layer (90° C., 2 h) is clearly seen as roughening of the surface (FIG. 4c). The HRSEM images (FIG. 4d-f) confirm that the 2D shape of the Au islands is not affected by the silica coating. No defects or cracks in the silica layer are seen on the length scale of FIG. 4. This is in agreement with the macroscopic CV results, the latter showing compete blocking of anion penetration through the porous silica layer (FIG. 3a).

Figure 5A:
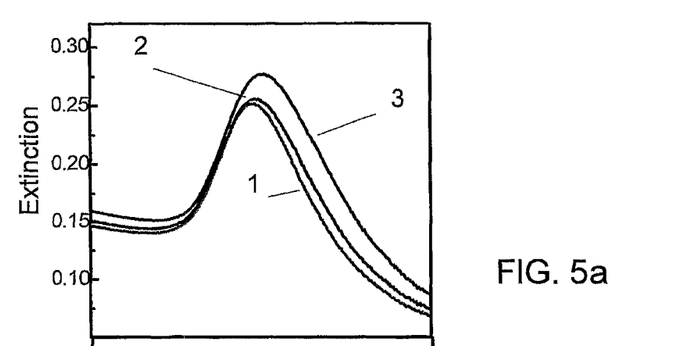

Formation of a silica layer on Au island films was studied by T-LSPR spectroscopy, monitoring changes in the SP absorbance. FIG. 5a shows UV-vis extinction spectra of a 5 nm Au island film, annealed, before (line 1) and after (line 2) MPTS adsorption, and after 2 h silica deposition at 90° C. (line 3). A change in the shape and intensity of the Au SP peak is seen after each step in the coating procedure, reflecting an increase in the effective refractive index of the Au islands' surrounding medium. The standard deviation of the differential intensity and the wavelength of maximum differential extinction are $1.2 \times 10^{-3}$ a.u. and 0.9 nm, respectively, both within the accuracy of the spectrophotometric measurement. For different batches the spread in the spectroscopic results is ca. ±0.01 a.u. and ±8.0 nm, respectively, reflecting certain variability in the preparation conditions. The reproducibility is expected to improve in automated preparation of silica-stabilized T-LSPR transducers.

The thickness of the silica layer on Au islands can be estimated using the distance dependence of T-LSPR spectra for the layer-by-layer preparation of coordination multilayers on Au island films [4,5]. Briefly, a bishydroxamate anchor SAM was prepared on Au, followed by binding of $Zr^{4+}$ ions to which a layer of ligand molecules comprising multidentate (2 or 3) bishydroxamate functional groups is coordinately bound. Additional sequential binding of $Zr^{4+}$ ions and multidentate organic ligands led to regular growth of multilayer films on both continuous and island-type Au films. The multilayer thickness, which increases incrementally with added layers, was measured on continuous Au substrate by several methods (ellipsometry, transmission spectroscopy, AFM, XPS). For a metal-organic bilayer comprising Au/bishydroxamate SAM+Zr(IV)+a tridentate layer, a thickness of 1.9 nm was determined [5]. The refractive index of the multilayer, obtained by modeling of the optical data, was $n_f=1.5$, $k_f=0$ [5].

Figure 5B:
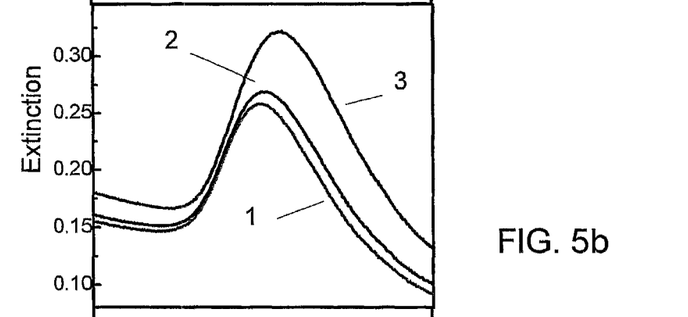
Figure 5C:
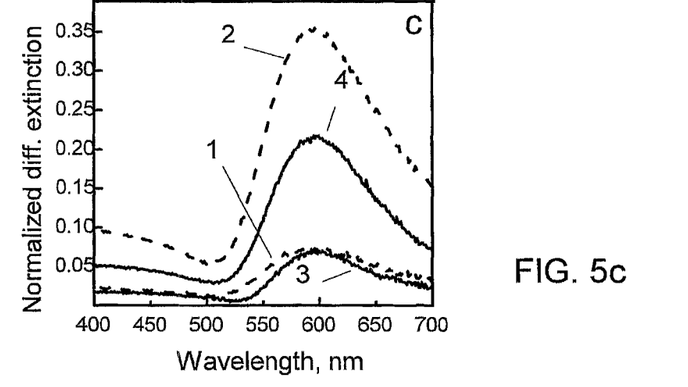

The morphology and optical properties (refractive index) of the silica and metal-organic multilayers on Au island films are similar; hence the thickness of the silica layer on the Au islands can be estimated from comparison of T-LSPR data for the two systems. T-LSPR spectra recorded after formation of a bishydroxamate SAM and after binding of $Zr^{4+}$ ions and a layer of the tridendate (hexahydroxamate) organic ligand are shown in FIG. 5b. Differential spectra (after subtraction of the bare Au spectrum) for the preparation of the silica film and the organic bilayer are presented in FIG. 5c. The difference spectra of the ligand monolayer (FIG. 5c, line 1) and the MPTS monolayer (FIG. 5c, line 3) are nearly identical, as expected. The spectrum of the silica layer (FIG. 5c, line 4) lies between those of the organic monolayer (FIG. 5c, line 1) and bilayer (FIG. 5c, line 2). Based on the known thicknesses of the coordinated layers [5] and the linear dependence of the maximum differential extinction on the overlayer thickness [4], the total thickness of the MPTS and the silica layer on the Au islands is estimated as ca. 1.2 nm. This value is in reasonable agreement with the thickness of ca. 1.5 nm measured ellipsometrically for the silica layer on a continuous Au film (see above).

Figure 6A:
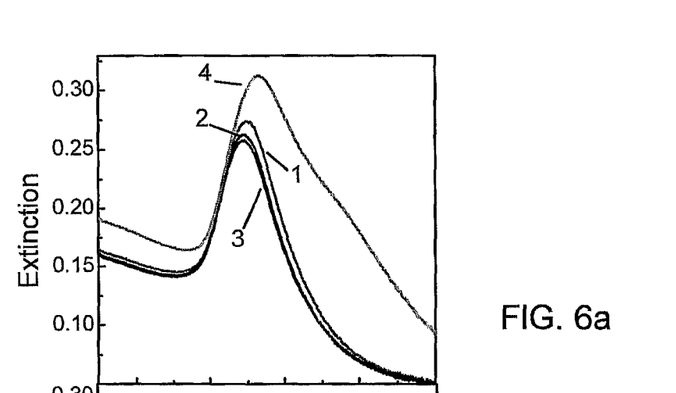

The stability of the Au SP absorbance toward immersion in various solvents (ethanol, methanol, water, PBS) and drying was tested with and without a silica coating on Au island films. Measurements were carried out in air, before and after dipping. For bare Au island films (FIG. 6a) the SP peak changes after immersion in each solvent. The most dramatic change is seen after dipping in PBS, the most common environment for biological sensing.

Figure 6B:
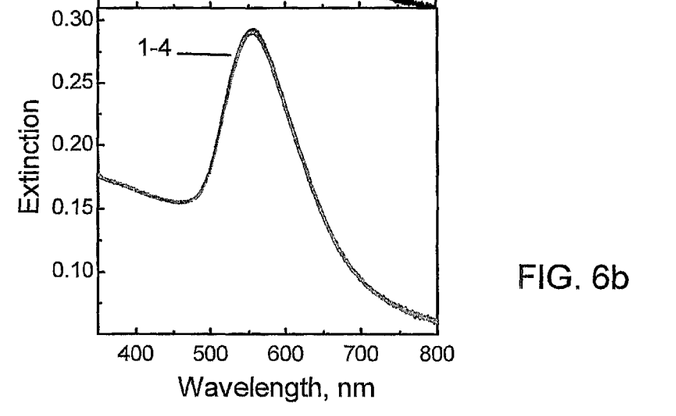

After coating of Au island films with a ca. 1.5 nm silica layer the stability of the optical response is dramatically improved (FIG. 6b). UV-vis spectra of silica-coated Au island films measured before and after immersion in all the solvents, including PBS, do not show any change in the SP absorbance within the accuracy of the measurement. This result establishes the feasibility of using silica-coated Au island films as transducers for chemical and biological sensing, ensuring that changes in the transmission spectra reflect solely binding/release of target analytes.

To demonstrate the application of silica-stabilized Au island films as optical transducers in T-LSPR sensing, the system sensitivity to binding of analytes to receptor layers on the silica coating was tested. The sensitivity of T-LSPR response of Au island films to remote analyte binding was previously shown [4]. Distance sensitivity of >15 nm was obtained with 5 nm Au island films, annealed. The same kind of Au islands, coated with silica, was used. Two types of analytes were chosen to demonstrate T-LSPR sensing: the dicarboxylate porphyrin PPIX and citrate-stabilized Ag NPs.

PPIX has an intense absorption band with a maximum at 400 nm and a molar extinction coefficient $\epsilon \sim 10^5$ $M^{-1}$ $cm^{-1}$ (FIG. 7a, line 4), allowing simultaneous monitoring of molecular absorption and changes in the Au SP band [2]. The SP absorbance of the Au island film around 550 nm is well separated from the PPIX molecular absorption band centered at 400 nm. For PPIX sensing, silica-coated Au island transducers were primed with a simulated receptor monolayer of the aminosilane APTS. Specific electrostatic binding of PPIX to APTS-modified samples was optically monitored, while unmodified samples (no APTS) were used as a nonspecific blank.

Figure 7A:
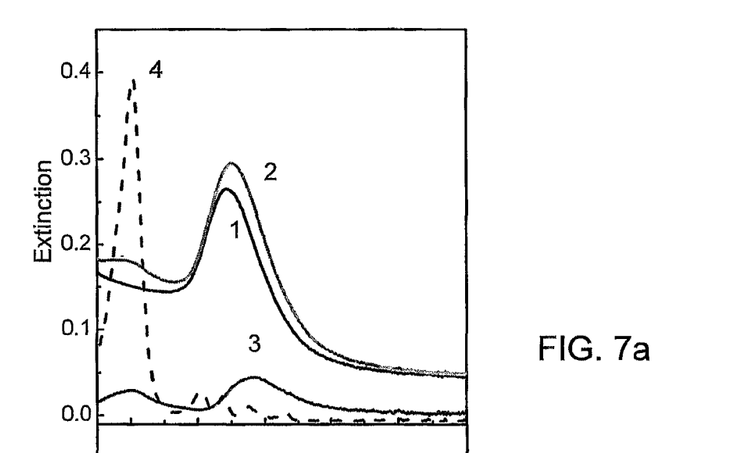
Figure 7B:
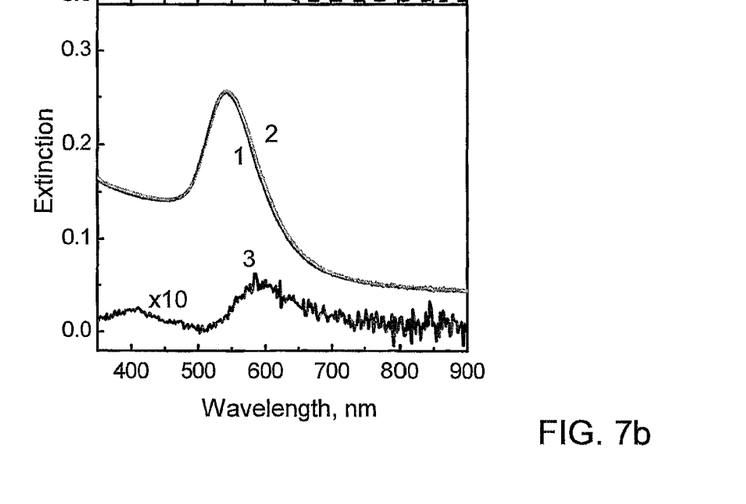

FIG. 7a shows extinction spectra of an APTS-modified, silica-coated transducer before and after binding of PPIX. The appearance of PPIX molecular absorbance and the change in the Au SP band are clearly seen in the extinction spectrum after PPIX binding (FIG. 7a, line 2) and particularly in the difference spectrum (FIG. 7a, line 3). The latter also shows that the wavelength of maximum absorbance of silica-bound PPIX is very close to that measured in ethanolic solution. In a control experiment using an unmodified (receptor-free) transducer, the spectra before and after exposure to PPIX nearly coincide (FIG. 7b, lines 1 and 2). Comparison of the differential spectra in FIG. 7a (line 3) and FIG. 7b (line 3, scaled ×10) reveals that the ratio between specific and non-specific adsorption is approximately an order-of-magnitude in favor of specific electrostatic binding.

The PPIX sensing experiments show a sub-monolayer sensitivity of silica-coated T-LSPR transducers, consistent with the previous results which demonstrated nearly constant sensitivity of the T-LSPR response to analyte binding up to more than 15 nm from the Au island surface [4]. Quantification can be achieved by measuring changes in one (or more) of several spectral parameters, i.e., maximum extinction intensity, wavelength of maximum extinction, or differential parameters [2].

Figure 8A:
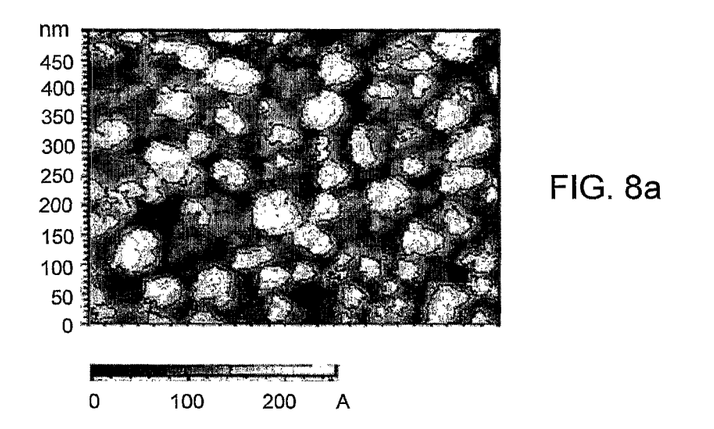
Figures 8B, 8C:
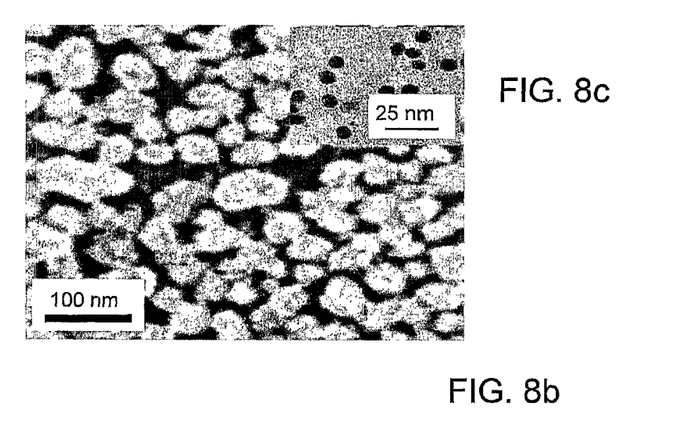

The sensitivity of the Au SP peak of silica-coated Au island transducers to changes in the dielectric properties of the immediate environment was also tested by electrostatic binding of Ag NPs: Negatively-charged, citrate-stabilized Ag NPs were bound to an APTS-modified silica overlayer on Au island film. Binding of the 9 nm (average diameter, see FIG. 8c) Ag NPs to the silica coating was examined by AFM and HRSEM imaging. FIG. 8 a,b shows images of an APTS-modified silica-coated Au island film after Ag NP binding. The Ag NPs are clearly seen immobilized on the surface of the Au islands in the AFM (as protrusions) and HRSEM (as bright spots) images. The limited resolution of the AFM and HRSEM precludes a definite conclusion regarding possible aggregation of some Ag NPs during sample drying. A small number of NPs are seen in the area between Au islands in the HRSEM image.

Figure 8D:
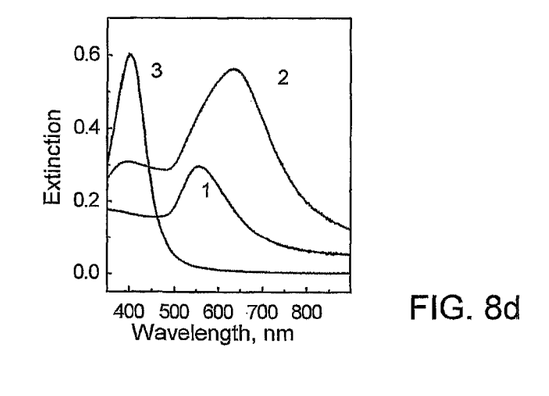
Figure 9A:
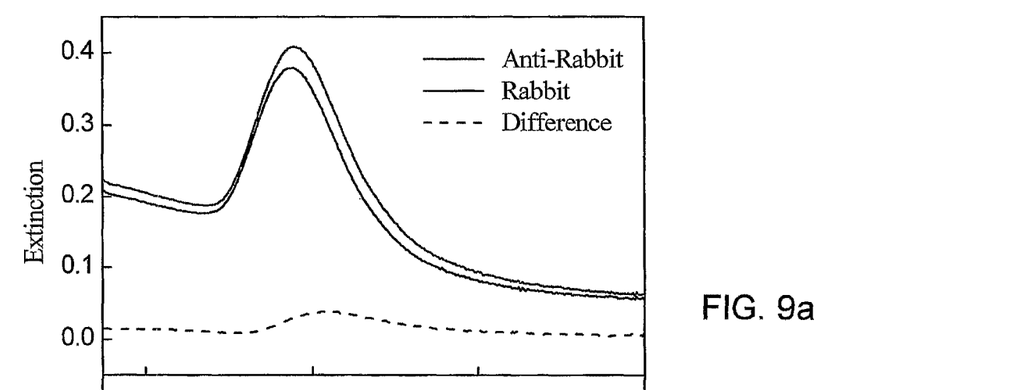
Figure 9B:
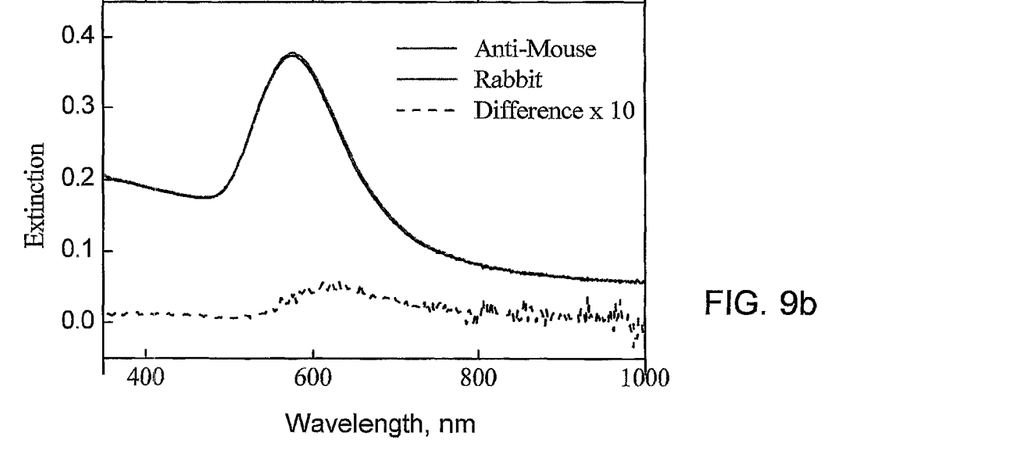
Figure 9C:
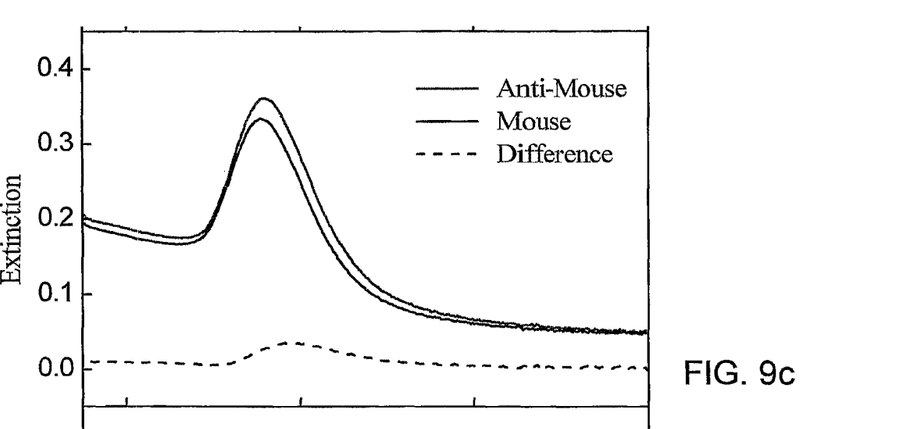
Figure 9D:
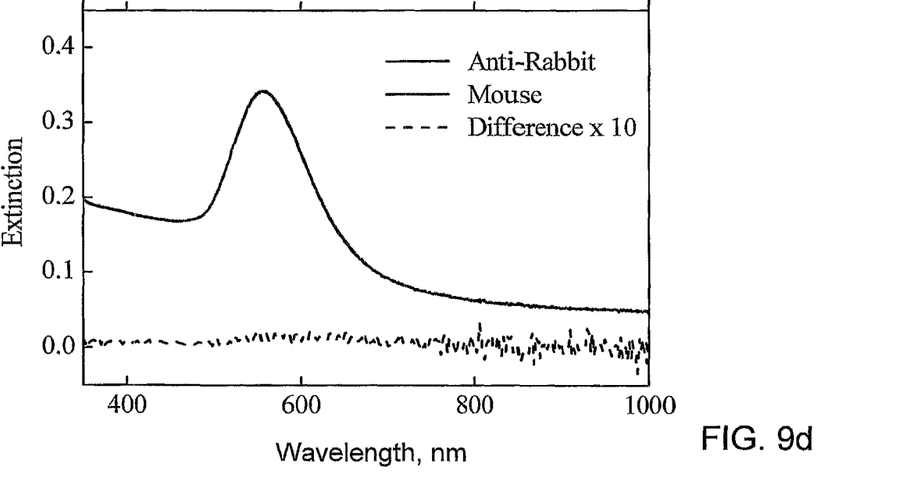

FIG. 8d shows changes in the extinction spectrum of a silica-coated Au island transducer induced by Ag NP binding to the APTS-modified silica overlayer. The small peak at 400 nm corresponds to the SP band of isolated Ag NPs between the Au islands, coinciding with the wavelength of the SP peak of the NPs in solution. The prominent effect of the Ag NPs on the extinction spectrum in the visible range is much greater than the dielectric response observed in the case of PPIX binding, suggesting coupling between the Au and Ag surface plasmons. Possible aggregation of Ag NPs during drying may also contribute to the SP plasmon band at 650 nm.

Example 2

Biological Sensing: Antigen-Antibody Interactions

The following example details the preparation of a substrate comprising a biological sensor and analyses of antigen-antibody interactions. Silica-coated Au substrates were extensively washed in methanol and modified with aminopropyltrimethoxysilane (APTS) by overnight immersion in a 10 v/% APTS solution in methanol. The coated slides were sonicated 3 times (5 min each) in methanol, washed with ethanol and dried under a stream of nitrogen. In order to get carboxylate functionalities, Au slides with APTS layer were washed with tetrahydrofuran (THF) for 20 min and then immersed for 4-5 h in deaerated freshly-prepared basic solution of succinic anhydride (reaction solution consisted of 0.1 g of succinic anhydride (Acros) and 400 μL of N,N-diisopropylethylamine (Aldrich) in 10 mL of dry THF). Then the slides were washed for 20 min in THF, dried under a stream of nitrogen and conditioned overnight in phosphate buffer saline (PBS) solution, prepared by 10-fold dilution of the commercial reagent GIBCO D-PBS (10×)-CaCl2,-MgCl2 (Invitrogen) with triply-distilled water. Similar PBS solution was used as a solvent throughout the antigen and antibody immobilization unless otherwise specified.

The immobilization of a specific receptor (antigen) was done as follows: Reaction between carboxylic groups of the interface (functionalized Au surface) and amine groups of the protein to form an amide bond was performed using 1-Ethyl-3-(3-dimethylaminopropyl)-carbodiimide (EDC, Danyel Biotech) and N-hydroxysuccinimide (NHS, Danyel Biotech). 30 µL mixture of EDC and NHS with final concentrations of 37.5 mg/mL and 5.75 mg/mL, respectively, was spread on an area of ~1 cm2 of the functionalized Au slides and left for 1 h in air at room temperature (22-23° C.). The slides were then washed in PBS for 20 min and dried under a stream of nitrogen. Next a stock solutions of 1 mg/mL immunoglobulin G (IgG) proteins from Rabbit or Murine (Mouse) serum (Sigma) were diluted with 0.3 M acetate buffer, pH=4.6 to a final concentration of 100 µg/mL. 30 µL of these solutions (Rabbit IgG or Mouse IgG) were spread on the surface of Au-coated slides (working area ~1 cm2) and left for 20 min in air at room temperature. Then slides were washed in PBS solution for 20 min and dried under a stream of nitrogen. In order to block unreacted carboxylic groups, the protein-derivatized Au films were treated with 1 M solution of ethanolamine hydrochloride, pH=8.5 (Danyel Biotech). 60 µL of this solution was spread on the slide surface as previously described, left for 20 min in air at room temperature, followed by washing for 20 min in PBS solution and drying under N2 stream. In order to prevent nonspecific binding during reaction with antibody and block uncoated spaces on the Au surface that left after immobilization of the antigen, protein-derivatized Au films were exposed to bovine serum albumin (BSA, Pentex) solution. 30 µL of 100 µg/mL BSA solution was spread on the Au surface as described above and left in air for 1 h at room temperature, followed by 20 min washing in PBS solution and drying under a stream of nitrogen. Samples prepared for UV-vis spectroscopy were rinsed with triply-distilled water before drying.

The antibody binding was performed as follows: stock solutions of 1 mg/mL of Anti-Rabbit IgG antibody produced in goat (Sigma) and stock solutions of 2 mg/mL of Anti-Mouse IgG antibody produced in goat (Sigma) were diluted with PBS to a final concentration of ~1*10−6 M. 30 µL of these antibody solutions (Anti-Rabbit IgG or Anti-Mouse IgG) were spread on the surface of antigen-derivatized Au surfaces (working area ~1 cm2) and left for 30 min in air at room temperature. The slides were then washed in PBS solution for 20 min and dried under a stream of nitrogen. Samples prepared for UV-vis spectroscopy were rinsed with triply-distilled water before drying.

The application of silica-modified nanoisland Au films as transducers for label-free recognition of biological molecules is demonstrated using selective antibody-antigen interactions. 5 nm Au island films (T-LSPR transducers) coated with a 1-2 nm silica layer were derivatized for use as interfaces for specific protein binding as detailed above. Rabbit and Mouse IgG proteins (antigens) and Anti-Rabbit and Anti-Mouse IgG proteins (antibodies) were used as objects for recognition of protein-protein interactions. In addition to high sensitivity in detecting antibody-antigen interactions, a crucial requirement of an effective immunosensor is selectivity, namely, differentiating between specific and nonspecific interactions. Reference is made to FIG. 9 representing transmission UV-vis (T-LSPR) spectra (absolute—solid lines, difference—dashed lines) for four different examples of antibody-antigen interactions (specific and nonspecific). In the case of specific binding (FIGS. 9a, 9c) significant increase of ~0.04 absorption units in plasmon peak intensity is observed, similar for both Rabbit—Anti-Rabbit (FIG. 9a) and Mouse-Anti-Mouse (FIG. 9c) interactions. In the two cases of nonspecific interactions, i.e., Rabbit-Anti-Mouse (FIG. 9b) and Mouse-Anti-Rabbit (FIG. 9d), almost no change in plasmon peak intensity is observed in the recognition step (see difference spectra in FIGS. 9b and 9d, multiplied ×10), pointing to minimal non-specific binding.

Thus, transmission localized surface plasmon resonance (T-LSPR) spectroscopy of evaporated Au island films presents a convenient platform for the construction of optical transducers for chemical and biological sensing. Formation of an ultrathin (~1.5 nm) layer of silica on the metal islands stabilizes the optical response toward immersion in solvents, while maintaining the transducer sensitivity to analyte binding. The ultrathin, uniform silica layer was deposited at 90° C. for 2 h from a sodium silicate solution onto Au surface (islands or continuous film) precoated with a mercaptosilane monolayer. Formation of the silica coating was studied by ellipsometry and XPS analysis, while the integrity of the layer was evaluated by measuring the transport of electroactive ions in electrochemical experiments. CV data show facile transport of cations ($Ru(NH_3)_6^{3+}$) and total blocking of anions ($Fe(CN)_6^{3-}$), consistent with a defect-free, negatively-charged nanoporous silica layer.

The optical properties of silica-coated Au island films are stable and virtually unaffected by interaction with solvents followed by drying, including PBS, an essential medium for biological applications. This allows preparation of T-LSPR recognition interfaces in which changes in the SP band are attributed exclusively to binding/release of analytes to/from the interface, fulfilling the basic requirement for sensing applications. The applicability and sensitivity of silica-coated Au island transducers were demonstrated by the detection of a porphyrin (PPIX) via electrostatic binding to a receptor layer on the silica surface, showing sub-monolayer sensitivity. Detection of Ag NP binding to a similar receptor layer on the silica revealed strong coupling of the Au and Ag surface plasmons. Silica-stabilized T-LSPR transducers present a general route to the development of a wide variety of stable and sensitive optical sensors. The same methodology may be applicable to transducers prepared by immobilization of metal NPs on surfaces.

While this invention has been particularly shown and described with references to preferred embodiments thereof, it will be understood by those skilled in the art that various changes in form and details may be made therein without departing from the scope of the invention encompassed by the appended claims.

What is claimed is:

1. A device for sensing an analyte in a surrounding medium comprising:
   a multi-layer structure comprising a solid transparent substrate having a sensing surface carrying an island film formed by a plurality of annealed discontinuous metal islands having smooth surfaces defining inherent optical property of the multi-layer structure for localized surface plasmon absorbance by the multi-layer structure,
   said annealed, smooth-surface and discontinuous metal islands being coated by an up to 10 nm ultrathin sol-gel derived silica film via self-assembled monolayer, thereby stabilizing said inherent optical property following exposure of said sensing surface to said surrounding medium, and enabling formation of binding sites highly sensitive to the analyte in the surrounding medium.

2. The device according to claim 1, wherein said self-assembled monolayer is of a compound having the general formula (I)

$$Z-R-SiO_{x/2}(OH)_{3-x}$$

Z being a binding moiety that can chemically associate with, attach to, or chemically sorb onto the metal, and R is a linker moiety.

3. The device according to claim 2, wherein Z is a sulfur containing moiety.

4. The device according to claim 2, wherein R is an aliphatic or aromatic moiety optionally substituted by a carboxy, carbonyl, amino, hydroxy or thio group.

5. The device according to claim 1, wherein said silica layer has a thickness of 0.5-3 nm.

6. The device according to claim 1, wherein the metal is gold.

7. The device according to claim 1, having stable optical properties and essentially unaffected following exposure to aqueous or organic solvents, washing and drying.

8. The device according to claim 7, wherein said optical properties are localized surface plasmon absorption.

9. The device according to claim 7, wherein changes in optical properties are essentially a consequence of binding or release of an analyte to/from a surface of the silica layer.

10. The device according to claim 9, wherein said surface comprises analyte binding sites.

11. A sensing device for sensing an analyte in a medium, the device comprising a device according to claim 9.

12. The device according to claim 1, configured and operable as a transmission localized surface plasmon resonance (T-LSPR) recognition interface in which changes in the SP band are attributed exclusively to binding/release of analytes to/from the interface, enabling sensing applications.

13. The device according to claim 12, configured and operable as a sensor based on T-LSPR mode and the optical response of said sensor is sensitive to changes in the effective dielectric constant of the immediate environment.

14. The device according to claim 12, wherein said sensor is configured and operable as an optical transducer for chemical and/or biological sensing.

15. The device according to claim 14, wherein said biological sensing comprises label-free recognition of biological molecules using selective antibody-antigen interactions.

16. The device according to claim 14, wherein said sensor is an immunosensor configured and operable to selectivity differentiating between specific and nonspecific interactions.

17. The device according to claim 12, wherein said silica layer is thin enough to afford high T-LSPR sensitivity, while the hydroxyl groups on its surface enable chemical modification for binding of receptor molecules.

18. The device of claim 1, wherein said multi-layer structure is manufactured by a process comprising:
    providing the solid transparent substrate;
    producing a metal island film on said substrate, said producing comprising depositing the metal and applying a post-deposition annealing at a predetermined annealing temperature selected to maintain desired adhesion of the metal islands to the substrate, thereby providing annealed discontinuous metal islands having smooth surfaces defining inherent optical property of the multi-layer structure for localized surface plasmon absorbance by the multi-layer structure;
    coating the islands with a monolayer of a compound having the general structure $Z-R-SiO_{x/2}(OH)_{3-x}$, Z being a binding moiety that can chemically associate with, attach to, or chemically sorb onto the noble metal and R is a linker moiety; and
    immersing the monolayer-coated substrate in a medium comprising a silica-based sol-gel precursor and providing conditions for a sol-gel reaction to yield a silica film over said monolayer, thereby stabilizing said inherent optical property following exposure of said sensing surface to said surrounding medium, and enabling formation of binding sites being highly sensitive to the analyte in the surrounding medium.

* * * * *